United States Patent
Pilat et al.

(10) Patent No.: US 9,435,725 B2
(45) Date of Patent: Sep. 6, 2016

(54) DEVICE, A SYSTEM AND A METHOD FOR MEASURING PERMEABILITY, IN PARTICULAR PERMEABILITY OF A FIBRIN CLOT

(71) Applicant: AKADEMIA GORNICZO-HUTNICZA IM. STANISLAWA STASZICA W KRAKOWIE, Cracow (PL)

(72) Inventors: Adam Pilat, Cracow (PL); Anetta Undas, Cracow (PL); Michal Zabczyk, Cracow (PL)

(73) Assignee: AKADEMIA GORNICZO-HUTNICZA IM. STANISLAWA STASZICA W KRAKOWIE, Cracow (PL)

( * ) Notice: Subject to any disclaimer, the term of this patent is extended or adjusted under 35 U.S.C. 154(b) by 303 days.

(21) Appl. No.: 14/133,684

(22) Filed: Dec. 19, 2013

(65) Prior Publication Data
US 2014/0174156 A1   Jun. 26, 2014

(30) Foreign Application Priority Data

Dec. 21, 2012 (PL) .......................... 402203

(51) Int. Cl.
*G01N 15/08* (2006.01)
*G01N 33/49* (2006.01)

(52) U.S. Cl.
CPC .......... *G01N 15/08* (2013.01); *G01N 15/0826* (2013.01); *G01N 33/4905* (2013.01)

(58) Field of Classification Search
CPC .......... A61M 2205/707; G01N 15/08; G01N 15/0826
See application file for complete search history.

(56) References Cited

U.S. PATENT DOCUMENTS

| 5,447,440 A * | 9/1995 | Davis | G01N 11/04 422/73 |
| 2002/0136836 A1* | 9/2002 | Denecke | G21G 1/06 427/402 |
| 2003/0045840 A1* | 3/2003 | Burko | A61M 5/1689 604/253 |
| 2003/0128267 A1* | 7/2003 | Teung | B01L 3/0265 347/112 |
| 2005/0203493 A1* | 9/2005 | Kuroda | A61M 1/16 606/5 |

(Continued)

FOREIGN PATENT DOCUMENTS

CN          101915724 A          12/2010

OTHER PUBLICATIONS

Wurfsus et al., "The Hydraulic Permeability of Blood Clots as a Function of Fibrin and Platelet Density", Biophsical Journal, vol. 104, Apr. 2013, pp. 1812-1823.*

(Continued)

*Primary Examiner* — David A Rogers
(74) *Attorney, Agent, or Firm* — Mark M. Friedman

(57) ABSTRACT

A device for measuring permeability of a material sample, the device comprising: an input tank (1) configured to store fluid and to supply the fluid to a sample tank (2) positioned below the input tank (1) and configured to hold the material sample, such as to allow the fluid from the input tank (1) to permeate through the material sample; a receptacle (25) positioned under the sample tank (2) to collect drops of fluid permeated through the material sample; and a device (3) for measuring the mass of the drops collected in the receptacle (25) and coupled with a controlling and monitoring device (11) configured to store data on measured mass and measurement times.

19 Claims, 3 Drawing Sheets

(56) References Cited

U.S. PATENT DOCUMENTS

| | | | | |
|---|---|---|---|---|
| 2006/0157408 A1* | 7/2006 | Kuroda | ............... | A61M 1/3639 210/636 |
| 2008/0147024 A1* | 6/2008 | Potts | ................... | A61F 13/4756 604/358 |
| 2009/0047440 A1* | 2/2009 | Giri | ......................... | B01L 3/022 427/457 |
| 2009/0297582 A1* | 12/2009 | Meyer | ............... | A61B 17/12022 424/423 |
| 2012/0296581 A1* | 11/2012 | Zhou | ...................... | B41J 2/0456 702/55 |

OTHER PUBLICATIONS

Abstract and Figure from Nikolaev et al., "Experimental Research on Fibrin Clot Permeability with Albumin Present", Moscow Universtity Physics Bulletin, vol. 64, Issue 3, Jun. 2009, pp. 324-328.*

Nikolaev et al., "Experimental Research on Fibrin Clot Permeability with Albumin Present", Moscow Universtity Physics Bulletin, vol. 64, Issue 3, Jun. 2009, pp. 324-328.*

Mills Joseph D et al: "Altered fibrin clot structure in the healthy relatives of patients with premature coronary artery disease", Circulation, vol. 106, No. 15, Oct. 8, 2002, pp. 1938-1942, XP002721400, issn: 0009-7322 *Fibrin Permeation Analysis; p. 1939, left-hand column*.

Database WPI Week Jan. 8, 2011 Thomson Scientific, London, GB; AN 2011-A38636 XP002721401, & CN 101 915 724 A (UNIV HEHAI) Dec. 15, 2010 *abstract*.

Young E W K et al; 'Technique for real-time measurements of endothelial permeability in a microfluidic membrane chip using laser-induced fluroescence detection' Analytical Chemistry 20100201 American Chemical Society USA, vol. 82, No. 3, Feb. 1, 2010, pp. 808-816, XP002721402, DOI:10.1021/AC901560W *figure 1*.

* cited by examiner

DEVICE, A SYSTEM AND A METHOD FOR MEASURING PERMEABILITY, IN PARTICULAR PERMEABILITY OF A FIBRIN CLOT

BACKGROUND OF THE INVENTION

1. Field of the Invention

The object of the invention is a device, a system and a method for measuring permeability, in particular permeability of a fibrin clot.

2. Description of the Related Art

Ischemia, a local blood supply disorder resulting from reduction or complete deficiency of blood supply in an organ or in a tissue caused by constriction or obstruction of its blood vessels, resulting in hypoxia, malnutrition and finally necrosis of the part of an organ suffering from ischemic process, is a frequent phenomenon in pathogenesis of many clinical conditions, as well as during performing surgical procedures. The causes of this phenomenon include, among others, formation of fibrin clots of abnormal stability and structure. Epidemiologic data obtained from ex vivo and in vitro studies indicate that the abnormal properties of fibrin clot are related to the occurrence of ischemic strokes, myocardial infarction or thromboembolic vascular disease. In general, the clots composed of dense network of thin fibrin fibres with tiny pores and high stability and resistance to enzymatic degradation, are related to the presence of prothrombotic state. Therefore, there are strong premises that the permeability of a fibrin clot can be a risk factor in the occurrence of thromboembolic events.

There are known methods for measuring permeability, for example by using Rowe's chamber. These methods involve assessing permeability and determining the coefficient of material permeability under a certain pressure of a flowing medium.

There is also known a device for assessing hydraulic permeability of hardening suspensions, described by FALACINSKI P., GARBULEWSKI K., KLEDYNSKI Z., SKUTNIK Z., ZIARKOWSKA A. 2004: "Badania barier hydraulicznych z zawiesin cementowo-bentonitowych z dodatkiem popiołów fluidalnych" ("Investigation of hydraulic barriers made of cement-bentonite suspensions with addition of fluidized ashes"), Przeglad Naukowy WIiKS, Yearbook XIII, Vol. 2/29, pp. 202-215.

The publication "A new optimized method for the determination of fibrin clot permeability" by Jonas A. Sjøland (*Lippincott Williams & Wilkins*, 2005, pp. 579-583) describes a system for measuring fibrin clot permeability, the system consisting of a glass vessel for fluid having a volume of 500 ml, equipped with a rubber stopper and a valve for levelling the pressure and a rubber hose connected to a polypropylene pipe (serologic pipette having the total volume of 1 ml, cut to a length allowing to fill it with 100 µl of material). The system is also equipped with a test tube (a receptacle), for collecting the fluid permeating through the fibrin clot and a stopwatch for measuring the permeation time. Use of such system requires a double measurement of the mass of the test tube—before and after the examination. Moreover, it is necessary to manually turn on and off the stopwatch, which is susceptible to the manual dexterity of the operator. Moreover, it is necessary to control the time lapse in order to stop collecting the permeate after a predetermined time (120 minutes to perfuse the clot and 110 minutes of measurement). A manual station requires the operator to monitor the level of a buffer in the tank due to its consumption, and weighing of the test tube used for the buffer permeated through the clot before and after the measurement. Thus, such measurement of permeability of a single clot is laborious and time consuming.

Besides, considering the fact that cardiovascular diseases are considered as the most frequent cause of death, and that the majority of diseases are related to the presence of prothrombotic state in blood vessels, there is a potential necessity to measure clot permeability as a routine test, which calls for utmost automation and simplification of the measurement.

Therefore, it would be advantageous to develop a method, a device and a system to automate and simplify the measurement of permeability, as well as to improve the quality of measurement.

SUMMARY OF THE INVENTION

The foregoing description presents a device for measuring permeability of a material sample, the device comprising: an input tank configured to store fluid and to supply the fluid to a sample tank positioned below the input tank and configured to hold the material sample, such as to allow the fluid from the input tank to permeate through the material sample; a receptacle positioned under the sample tank to collect drops of fluid permeated through the material sample; and a device for measuring the mass of the drops collected in the receptacle and coupled with a controlling and monitoring device configured to store data on measured mass and measurement times.

Preferably, the device further comprises: a pump connected to a hose for supplying fluid from a feeding tank to the input tank; wherein the controlling and monitoring device is further configured to control the pump to supply fluid from the feeding tank to the input tank in an amount corresponding to the weight of the drop collected in the receptacle.

Preferably, the device further comprises a distance measuring element positioned under the receptacle and a distance sensor located coaxially with the vertical axis below the distance measuring element.

Preferably, the input tank is connected to the sample tank a coupling selected from a group consisting of: a silicone connecting holder, a threaded coupling, a magnetic coupling, a sleeve with a vent valve.

Preferably, the receptacle comprises openings in side walls.

Preferably, the receptacle has a conical shape.

Preferably, the sample tank and held inside an electromagnet core by electromagnetic force.

Preferably, the device further comprises a sensor of temperature of electromagnet winding.

Preferably, the device further comprises a sensor of temperature of electromagnet core.

Preferably, the receptacle has a conical shape and comprises a ring made of ferromagnetic material or a magnet of vertical polarization.

Preferably, the receptacle is equipped with a permanent magnet located in the bottom part of the receptacle.

Preferably, the device further comprises a magnetic field sensor located in the gap between the electromagnet and the receptacle.

Preferably, the magnetic field sensor is a Hall sensor.

Preferably, the controlling and monitoring device comprises a distance sensor connected to a receptacle position locator being connected to a regulator equipped with one output connected to a data exchange block and the second output connected to a power controller; the power controller having a first output connected to an electromagnet winding and at least one second output connected in a feedback with the regulator.

Preferably, the controlling and monitoring device comprises a magnetic field sensor connected to a receptacle position locator being connected to the regulator having one output connected to the power controller, the power controller having a first output connected to the electromagnet winding, and at least one output connected in a feedback with the regulator.

Preferably, the controlling and monitoring device comprises a temperature detector whose inputs are connected to a sensor of temperature of electromagnet winding, a sensor of temperature of electromagnet core and an external temperature sensor.

Further, there is presented a system for measuring permeability of a material sample, comprising the abovementioned device, wherein the controlling and monitoring device is connected to a recording and analyzing device configured to record and analyze data in real-time.

Preferably, the device for measuring permeability of a material sample is located in a climatic chamber.

Preferably, the system further comprises an image recording device directed towards the sample and connected to the controlling and monitoring device.

There is further presented a method for measuring material permeability, comprising the steps of: providing a device as described above; analysing the measured mass and measurement times for individual drops to determine the permeability of material stored in the sample tank.

Preferably, the method further comprises feeding the input tank with an amount of fluid providing a constant hydrostatic pressure influencing the measured material in the sample tank by the fluid from the input tank.

The device may further comprise an image recording device to record the condensation phenomenon, the image recording device being connected to the controlling and monitoring device in order to record the image at selected time points.

A climatic chamber shall be understood as a room with specific climatic conditions, in particular as a room with controlled conditions, as an enclosure of a post with climate parameters control system or as a commercial climatic chamber in which the measurement is performed. The status of climatic conditions is recorded by a measuring and controlling device.

The weighing device utilizing an active magnetic levitation technology measures the mass by analysing measurement signals in the levitation system.

For example, estimation of mass can be performed on the basis of the position of the levitating tank, the intensity of current flowing through a winding of an electromagnetic actuator, as well as the known parameters and characteristics of the device.

Detection of mass is performed by using one or more of the following methods, depending on the type of control.

The distance and current intensity can be measured in a electromagnetic actuator. A receptacle position sensor is located under the receptacle and connected to a regulator via a receptacle position locator. The regulator controls the electromagnet by a power controller.

Another method for measuring mass involves measurement of voltage and current in an electromagnetic actuator by using a sensor of electromagnet winding supply voltage and a sensor of current flowing in the electromagnet winding, the sensors being located in the power controller and connected, respectively, to the regulator via outputs Out2 and Out3. The regulator determines control parameters for the electromagnet and provides them to the power controller.

Yet another method involves measuring the magnetic field in a gap between the actuator and the levitating scale pan. A magnetic field sensor is located in the gap between the front of the electromagnet and the receptacle and connected to a magnetic field detector. A sensor of current flowing through the electromagnet winding is located in the power controller and connected via output Out3 to the regulator. The regulator stabilizes the receptacle on the basis of the changes of electromagnetic field and the current intensity, by calculating the control signal and providing it to the power controller, which relays the signal to the input of the electromagnet.

It is also possible to measure magnetic field below the scale pan using a magnet fixed at the bottom end of the pan. The magnetic field sensor is connected to a magnetic field detector. A sensor of current flowing through the electromagnet winding is located in the power controller and connected via output Out3 to the regulator. The regulator stabilizes the receptacle on the basis of the changes of electromagnetic field and the current intensity, by calculating the control signal and providing it to the power controller, which relays the signal to the input of the electromagnet.

The presented device and method allows to eliminate the necessity of weighing the receptacle collecting the permeate before and after the measurement, by utilising the device for measuring mass having the receptacle as an integral part of the system, which eliminates measurement errors.

Additionally, due to the device for measuring mass based on levitation technology, the precision of time measurement is increased, while the range of minimal measurable mass is reduced (nano-, micro- and milligrams). Besides, it is possible to continuously record parameters, especially time and mass, as well as to operate under variable environmental conditions.

Apart from automation of measurement, the presented system and method further allow to reduce the clot perfusion time to an indispensable minimum, that is until the drops of buffer permeating through the clot are characterized by identical mass (within a measurement tolerance), and the time measured between settling of the previous and the current drop is identical (within a measurement tolerance) or the mass/time relation reaches a plateau while running in a linear way.

Besides, the number of drops and the time necessary for complete clot perfusion have been significantly minimized in comparison to the prior art solutions.

An additional advantage of the presented device and method is the possibility of materials of extreme permeability values, in particular measuring materials of extremely low permeability, wherein the perfusion time exceeds 100 minutes and manual measurement would be burdened with error.

Furthermore, it is possible to perform a long time analysis without losing measurement precision. Measurement of material properties is performed on the basis of simultaneous recording of condensation time and drop mass and the change of these parameters.

In addition, use of the mass measuring device based on levitation technology, makes it possible to increase the precision of time measurement, while reducing the range of minimal measurable mass (nano-, micro- and milligrams). Besides, it is possible to continuously measure parameters, in particular time and mass, as well as to operate under variable environmental conditions.

BRIEF DESCRIPTION OF DRAWINGS

The device, system and method are shown by means of example embodiments on a drawing, wherein:

FIG. 2 shows a device for measuring mass of the permeated fluid utilizing an active levitation technology, indicating the location of a magnetic field sensor FIG. 2a;

DETAILED DESCRIPTION OF THE PREFERRED EMBODIMENTS

Figure 1:
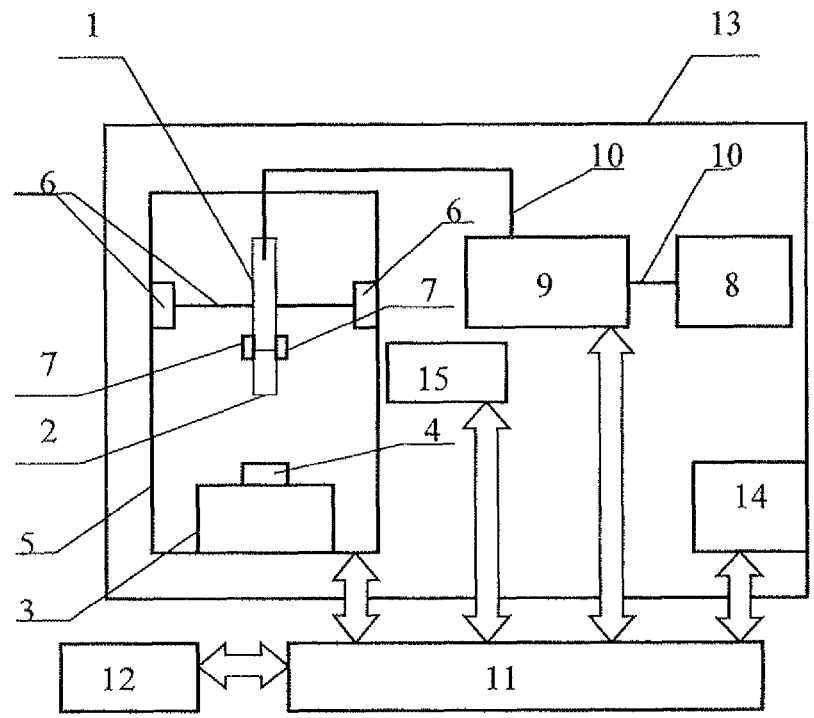
FIG. 1 shows a system for measuring permeability.
Figures 2, 2A:
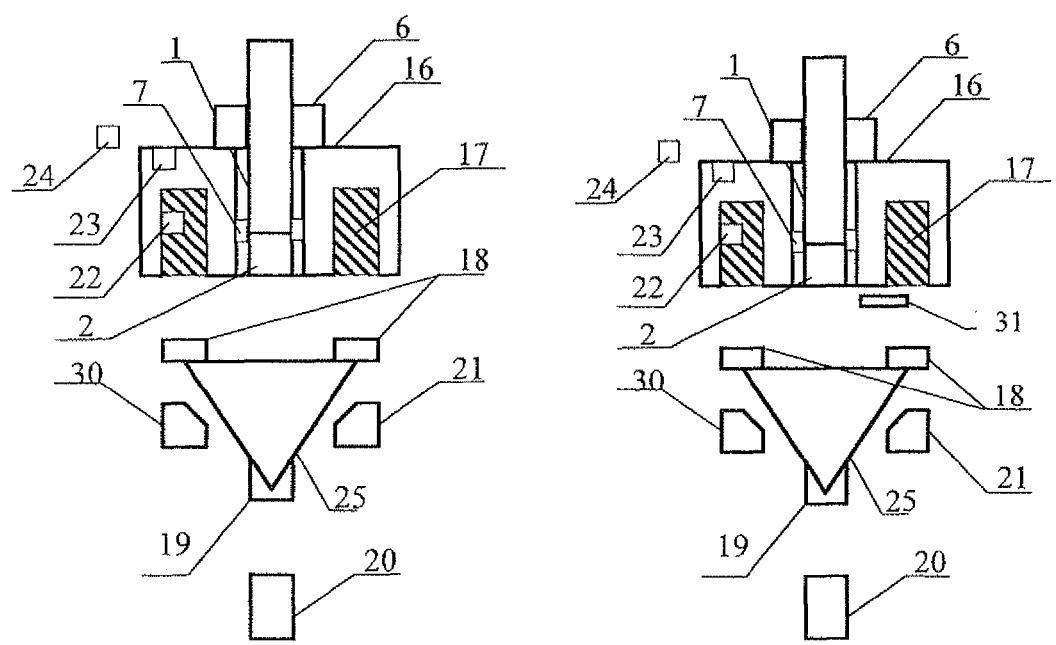
Figure 3:
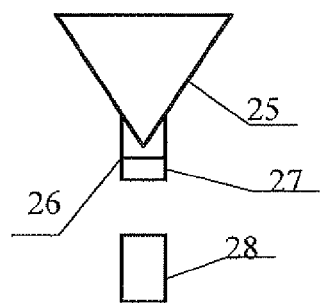
FIG. 3 shows a configuration of a receptacle of the device for measuring mass by magnetic field sensor, utilizing the active levitation technology.

The system for measuring permeability comprises a device 3 for measuring mass of permeated fluid connected with a real-time controlling and monitoring device 11 which, by controlling a pump 9, allows for precise batching and automatic supplementing of fluid level in an input tank 1. The fluid is permeated through an examined sample, which is located in a sample tank 2 and drips into a receptacle 4, located in a climatic chamber 13. The control device 11 batches a portion of fluid, corresponding to the volume of one drop, from a feeding tank 8 to the input tank 1. The device 3 for measuring mass registers its change in a continuous way using the controlling and monitoring device 11, and the results are collected by a recording and analyzing device 12. The device 3 for measuring mass can be calibrated on a request sent by the controlling and monitoring device 11. The parameters of the material are determined by software on the basis of the collected measurement data. During registration of mass change by the controlling and monitoring device 11, the pump 9 automatically batches a proper volume of fluid through the silicone hose 10. The mass of the fluid permeated through the sample is controlled and the time between falling of the previous and the present drop measured. The measurement is completed on reaching the set time or a set number of drops or a set number of drops after achieving the perfusion condition.

The input tank 1 connected with the sample tank 2 is located in the axis of the device 3 for measuring mass of the permeated fluid at a specified height above the receptacle 4, 25. The height is set manually or automatically by a holder 6. The input tank is filled up to height H in order to obtain pressure P influencing the sample. The pressure depends on the resistance of the examined material.

The system which comprises the pump 9 for drawing fluid from the feeding tank and controlled by the controlling and monitoring device 11, ensures constant fluid volume in the input tank 1. This guarantees maintaining uniform measurement conditions during the entire duration of the process.

Figure 4:
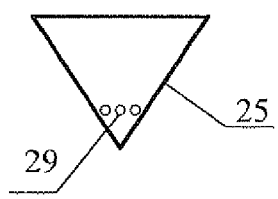
FIG. 4 shows an embodiment of the receptacle with openings.
Figure 5:
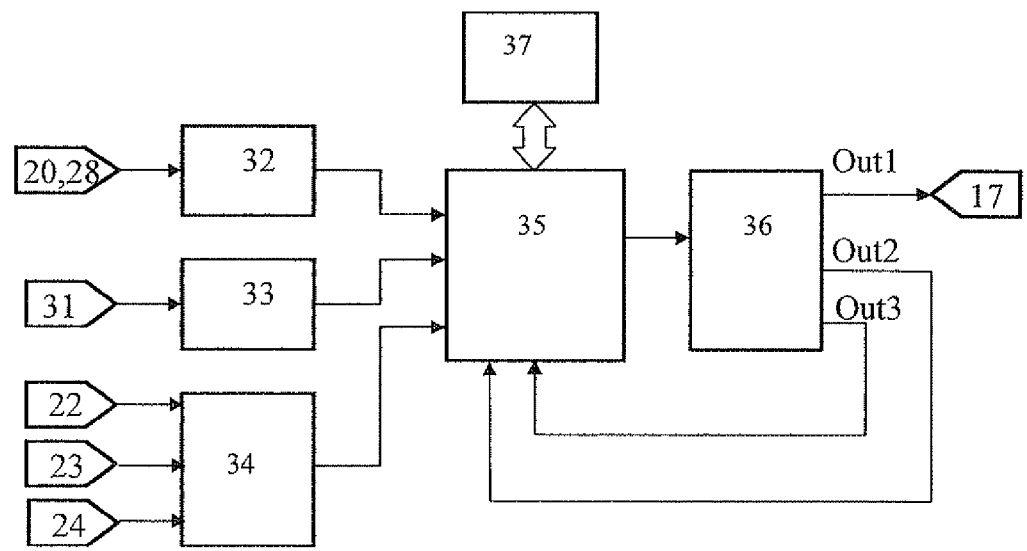
FIG. 5 shows a real-time controlling and monitoring device.

The receptacle 4, 25 has a conical shape and is located inside the device 3 for measuring mass of the permeated fluid. It levitates contactlessly in case the device for mass measurement utilizes levitation technology. The receptacle 4, 25 is a vessel having hermetic bottom and side walls, while the upper part is completely or partially open it comprises an opening through which the drops enter. The receptacle, as shown in FIG. 4, may have openings 29 for ensuring a constant fluid level.

A sample, prepared previously by putting a certain volume of the examined material in the sample tank 2, is placed in the input tank 1, using a silicone coupling, such as to avoid creation of air bubbles in this part of the device. The volume of the examined material can be from 0.001 µl to 1 l, and in particular it is 100 µl of a congealing citrate plasma placed in the sample tank 2, which can be made of polypropylene and have the volume from 0.001 µl to 1 µl; in particular, the sample tank 2 is a tank having a diameter of 2.8 mm and a length of 18 mm, with threaded or tarnished internal walls. The input tank 1 with the sample is then mounted on a stand 5 located in the vertical axis of the scales; next, the outlet of the pump 9 hose is immersed in the input tank 1, while the inlet of the pump 9 hose is placed in the feeding tank 8. Using a scale on the input tank 1, a volume of fluid which will allow for maintaining a hydrostatic pressure corresponding to a 4 cm water column, influencing the examined material between the meniscus of the fluid in the input tank and the bottom edge of the pipe containing material, is batched by the pump 9. The climatic chamber 13 is closed after precise setting of all elements. The temperature in the climatic chamber 13 can range from −100° C. to 150° C., while the pressure can be regulated with the accuracy of 1 atm±50%. In a particular embodiment, the climatic chamber maintains a set and constant temperature of 22° C. as well as a set and constant pressure of 1 atm during the procedure. The fluid, which then drips into the receptacle 4, 25, flows spontaneously through the examined material. The device 3 for measuring mass registers change of the mass of the receptacle 4, 25 related to a drop falling from the sample tank 2 and the result is recorded by the control-monitoring device. A peristaltic pump batches automatically a suitable amount of fluid through a silicone hose, during registration of the mass change.

A device for measuring mass of the permeated fluid utilizing the levitation technology according to the invention, measures mass in the receptacle 4, 25 by registering changes of: a signal from a distance sensor 30 indicating the position of the tank, a signal from the output Out1 indicating the intensity of current in an electromagnet winding 17, as well as the characteristics and parameters of the device. A regulator 35 stabilizes the tank.

There are also possible other types of construction of the device 3 for measuring mass of the permeated fluid, depending on the control system which is used.

The electromagnet of the scales comprises a core 16 and a winding 17 for generating the magnetic field for levitating the receptacle 4, 25. The electrodynamic force influences ferromagnetic/magnetic elements 18 of the tank. In the release state, the receptacle 4, 25 is supported by holders 21. A central opening in the electromagnet core 16 is intended for placement of the tank 1 with the sample tank 2, which are positioned and mounted by a holder 7.

In order to measure the distance and the current intensity in the electromagnetic actuator, a sensor of position of the receptacle 4, 25, located under the receptacle, is connected to the regulator 35 via a receptacle position locator 32. The regulator 35 controls the electromagnet 16, 17 via a power controller 36.

In order to measure the voltage and current in the electromagnetic actuator, a sensor of the electromagnet winding 17 supply voltage of and a sensor of the electromagnet winding 17 current intensity, located in the power controller 36, are connected to the regulator 35, respectively, via outputs Out2 and Out3. The regulator 35 controls the electromagnet and feeds the control parameters to the power controller 36.

In order to measure the magnetic field in the gap between the electromagnetic actuator and the levitating scale pan, a magnetic field sensor 31, located in the gap between the front of the electromagnet 16 and the receptacle 4, 25, is connected to a magnetic field detector 33. The regulator 35 stabilizes the receptacle 4, 25 on the basis of changes of the magnetic field by calculating the control signal and providing it to the power controller 36, which feeds the signal to the electromagnet winding inputs 17.

In order to measure the magnetic field below the scale pan using a magnet fixed at the bottom of the pan, a magnetic field sensor 28 is connected to the magnetic field detector 33. The regulator 35 stabilizes the receptacle 4, 25 on the basis of magnetic field changes, calculates control parameters and feeds them to the power controller 36 which, in turn, relays the signal to the inputs of the electromagnet 16.

Continuous recording of time and mass measured by the device 3 for measuring mass of the permeated fluid allows for precise measurement of condensation time, due to the reaction of the mass measuring device to change of mass in the receptacle. Continuous recording also allows for observation of the device operation and of the measurement procedure, until reaching a constant value.

Figure 6:
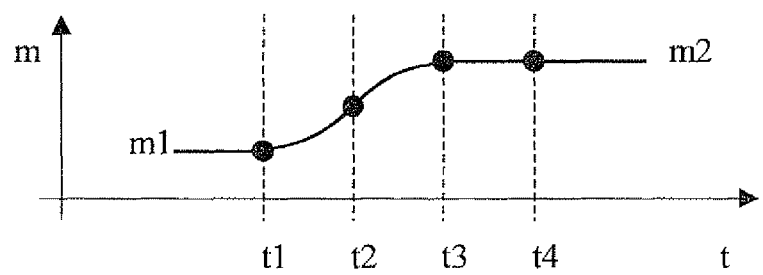
FIG. 6 shows recording of a mass of a drop.

The mass of a drop is established by measurement of the difference between the masses m2 and m1. The times t1, t2, t3 and t4 characteristic for the event are measured. The time t1 determines the occurrence of mass measurement event and beginning of registration of mass change. The time t2 is the middle point between the times t1 and t3. The time t3 is the point of time when mass measurement has been completed. The period t3, t4 is the time interval during which no mass change occurred FIG. 6.

The drop mass is registered continuously and it may comprise the following stages:
a) the state of the mass measuring device before the fall of the drop—recording the initial mass m1,
b) the occurrence of the event of a drop fall on the scale pan—time t1—the weighing process begins,
c) a transient state—weighing—time t2,
d) the end of mass stabilization—time t3—weighing result—mass m2,
e) stable measurement of mass during the period t3, t4—mass m2.

The result of the measurement is the value of the mass m2, obtained during the time interval t3, t4 within an admissible measurement tolerance.

Figure 7:
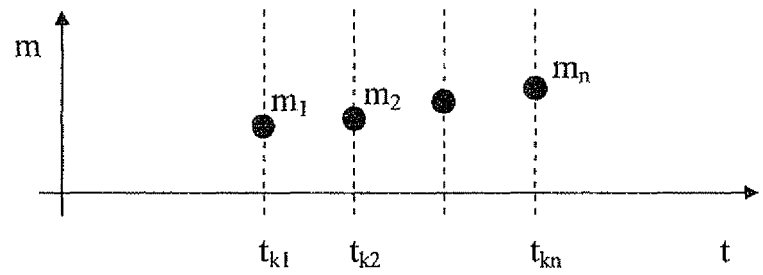
FIG. 7 shows recording of a mass of subsequent drops.

In order to determine properties of a material, the times $t_{k1}$, $t_{k2}$, $t_{k3}$, for which masses of drops $m_1$, $m_2$, $m_3$, ..., $m_n$ FIG. 7 have been recorded, are used. Measurement of clot permeability is a special case, due to presence of proteins and pigments contained in the plasma, which should be washed out before beginning of the measurement. After the was out, the fibrin clot assumes the form of a flexible body of a high viscosity gel and of a porous structure. Research has shown that a flexible gel needs to be stabilized in order to obtain a constant mass increase in time—plateau stage $t_{k1}$ up to $t_{kn}$ with mass from $m_{k1}$ up to $m_{kn}$—because of arrangement of fibrin fibres consistent with the flow direction. The permeability measurement is effected on the basis of mass differences $m_{km}-m_{kn}$ over time $t_{km}-t_{kn}$ and constant values, such as the length of the clot, section surface, drop volume calculated on the basis of buffer density, buffer viscosity and hydrostatic pressure value. Additional parameters, such as the number of drops necessary for complete perfusion and stabilization of the flexible clot, as well as the time necessary for complete perfusion of the clot, were distinguished on the basis of the possibility of constant monitoring of mass changes in time. A fibrin clot of a low permeability is characterized by a long time necessary for complete perfusion. A fibrin clot of a high permeability is characterized by a short time necessary for complete perfusion. Thus, the number of drops necessary for complete perfusion depends on the time required for complete perfusion, clot flexibility, as well as concentrations of the substances dissolved in plasma. A clot of a low permeability is composed of a dense network of thin and rigid fibrin fibres with small pores between them, which makes it difficult for enzymatic digestion with lytic enzymes physiological and therapeutic. A clot of a high permeability is composed of thick, flexible fibres with large pores between them. It has been proven that clot permeability is significantly reduced in comparison to a healthy control group in many pathologies related to the increased risk of cardiovascular events. The measurement of clot permeability also allows for evaluation of drug influence on the fibrin network as well as other factors, which might potentially influence the permeability.

The invention claimed is:

1. A device for measuring a permeability of a material sample, the device comprising:
an input tank configured to store a fluid and to supply the fluid to a sample tank positioned below the input tank and configured to hold the material sample, such as to allow the fluid from the input tank to permeate through the material sample;
a receptacle positioned under the sample tank to collect drops of the fluid permeated through the material sample; and
a mass measuring device for measuring a mass of the drops collected in the receptacle and coupled with a controlling and monitoring device configured to store data on the measured mass and measurement times; and,
an electromagnet core for producing an electromagnetic force for holding the sample tank at least partially within the electromagnet core.

2. The device according to claim 1, further comprising:
a pump connected to a hose for supplying the fluid from a feeding tank to the input tank;
wherein the controlling and monitoring device is further configured to control the pump to supply the fluid from the feeding tank to the input tank in an amount corresponding to the mass of the drops collected in the receptacle.

3. The device according to claim 1, further comprising a distance measuring element positioned under the receptacle and a distance sensor located coaxially with the vertical axis below the distance measuring element.

4. The device according to claim 1, wherein the receptacle comprises openings in side walls.

5. The device according to claim 1, wherein the receptacle has a conical shape.

6. The device according to claim 1, further comprising a sensor of a temperature of an electromagnet winding.

7. The device according to claim 1, further comprising a sensor of a temperature of the electromagnet core.

8. The device according to claim 1, wherein the receptacle has a conical shape and comprises a ring made of a ferromagnetic material or a magnet of a vertical polarization.

9. The device according to claim 8, wherein the receptacle has a permanent magnet located in a bottom part of the receptacle.

10. The device according to claim 8, further comprising a magnetic field sensor located in a gap between the electromagnet core and the receptacle.

11. The device according to claim 10, wherein the magnetic field sensor is a Hall sensor.

12. The device according to claim 1, wherein the controlling and monitoring device comprises a distance sensor connected to a receptacle position locator being connected to a regulator having a first output connected to a data exchange block and a second output connected to a power controller: the power controller having a first output connected to an electromagnet winding and at least one second output connected in a feedback with the regulator.

13. The device according to claim 1, wherein the controlling and monitoring device comprises a magnetic field sensor connected to a receptacle position locator being connected to a regulator having an output connected to a power controller, the power controller having a first output connected to an electromagnet winding, and at least one second output connected in a feedback with the regulator.

14. The device according to claim 1, wherein the controlling and monitoring device comprises a temperature detector having inputs connected to a sensor of a temperature of an electromagnet winding, a sensor of a temperature of the electromagnet core and an external temperature sensor.

15. A system for measuring a permeability of a material sample, the system comprising:
a permeability measuring device comprising:
an input tank configured to store a fluid and to supply the fluid to a sample tank positioned below the input tank and configured to hold the material sample, such as to allow the fluid from the input tank to permeate through the material sample;
a receptacle positioned under the sample tank to collect drops of the fluid permeated through the material sample; and
a mass measuring device for measuring a mass of the drops collected in the receptacle and coupled with a controlling and monitoring device configured to store data on the measured mass and measurement times; and,
an electromagnet core for producing an electromagnetic force for holding the sample tank at least partially within the electromagnet core; and,
wherein the controlling and monitoring device is connected to a recording and analyzing device configured to record and analyze data in real-time.

16. The system according to claim 15, wherein the permeability measuring device is located in a climatic chamber.

17. The system according to claim 15, further comprising an image recording device directed towards the sample and connected to the controlling and monitoring device.

18. A method for measuring a permeability of a material, the method comprising the steps of:
providing a permeability measuring device comprising:
an input tank configured to store a fluid and to supply the fluid to a sample tank positioned below the input tank and configured to hold the material sample, such as to allow the fluid from the input tank to permeate through the material sample;
a receptacle positioned under the sample tank to collect drops of the fluid permeated through the material sample;
a mass measuring device for measuring a mass of the drops collected in the receptacle and coupled with a controlling and monitoring device configured to store data on the measured mass and measurement times; and,
an electromagnet core for producing an electromagnetic force for holding the sample tank at least partially within the electromagnet core; and,
analyzing the measured mass and measurement times for individual drops to determine the permeability of the material stored in the sample tank.

19. The method according to claim 18, further comprising: feeding the input tank with an amount of the fluid providing a constant hydrostatic pressure influencing the measured material in the sample tank by the fluid from the input tank.

* * * * *